United States Patent
Buffel et al.

(10) Patent No.: US 10,195,295 B2
(45) Date of Patent: Feb. 5, 2019

(54) PROCESS FOR PURIFYING 1,4,7,10-TETRA-AZACYCLODODECANE-1,4,7,10-TETRAACETIC ACID

(71) Applicant: T2Pharma GmbH, Weimar (DE)

(72) Inventors: Diederik Buffel, Mortsel (BE); Xavier Boi, Mortsel (BE); Judith Pype, Mortsel (BE)

(73) Assignee: T2PHARMA GMBH, Weimar (DE)

( * ) Notice: Subject to any disclaimer, the term of this patent is extended or adjusted under 35 U.S.C. 154(b) by 155 days.

(21) Appl. No.: 15/116,263

(22) PCT Filed: Feb. 2, 2015

(86) PCT No.: PCT/EP2015/052033
§ 371 (c)(1),
(2) Date: Aug. 3, 2016

(87) PCT Pub. No.: WO2015/117911
PCT Pub. Date: Aug. 13, 2015

(65) Prior Publication Data
US 2017/0007726 A1  Jan. 12, 2017

(30) Foreign Application Priority Data
Feb. 6, 2014 (EP) .................... 14154106

(51) Int. Cl.
| | | |
|---|---|---|
| *A61K 49/00* | (2006.01) | |
| *A61K 47/18* | (2017.01) | |
| *A61K 49/10* | (2006.01) | |
| *C07D 257/02* | (2006.01) | |
| *B01D 61/02* | (2006.01) | |
| *C07D 295/15* | (2006.01) | |
| *C07F 5/00* | (2006.01) | |

(52) U.S. Cl.
CPC ............ *A61K 49/108* (2013.01); *A61K 47/18* (2013.01); *B01D 61/027* (2013.01); *C07D 257/02* (2013.01); *C07D 295/15* (2013.01); *C07F 5/003* (2013.01); *B01D 2311/2649* (2013.01); *B01D 2311/2673* (2013.01); *B01D 2315/16* (2013.01)

(58) Field of Classification Search
CPC .................................. A61K 49/00; A61K 47/00
See application file for complete search history.

(56) References Cited

U.S. PATENT DOCUMENTS

| | | | | |
|---|---|---|---|---|
| 2014/0323719 A1* | 10/2014 | Rangisetty | ............ | C07C 227/40 540/474 |
| 2015/0259304 A1* | 9/2015 | Moore | ................. | C07D 257/02 540/474 |

FOREIGN PATENT DOCUMENTS

| | | |
|---|---|---|
| WO | 98/56775 A1 | 12/1998 |
| WO | WO-9856775 | * 12/1998 |
| WO | 99/05128 A1 | 2/1999 |
| WO | 2011/054480 A1 | 5/2011 |
| WO | 2013/076743 A2 | 5/2013 |
| WO | 2014/114664 A1 | 7/2014 |

OTHER PUBLICATIONS

Nanofiltration EMIS-2010 (Year: 2010).*
Official Communication issued in International Patent Application No. PCT/EP2015/052033, dated Mar. 10, 2015.
Stetter et al., "Complex Formation with Tetraazacycloalkane-N,N',N",N'"—Tetraacetic Acids as a Function of Ring Size," Angewandte Chemie International Edition in English, vol. 15, No. 11, 1976, pp. 686.
Clarke et al., "Stabilities of the Alkaline Earth and Divalent Transition Metal Complexes of the Tetraazamacrocyclic Tetraacetic Acid Ligands," Inorganics Chimica Acta, 190, 1991, pp. 27-36.
Hernandez et al., "Proton Magnetic Relaxation Dispersion in Aqueous Glycerol Solutions of Gd(DTPA)2- and Gd(DOTA)-" Inorg. Chem., vol. 29, 1990, pp. 5109-5113.
Van Der Bruggen et al., "Nanofiltration", chapter 11, Advanced Membrane Technology and Applications, 2008, pp. 271-295.
Sorin et al., "Polyaminocarboxylic acids rejection by charged nanofiltration membrane", Journal of Membrane Science, vol. 279, 2006, pp. 446-452.

* cited by examiner

Primary Examiner — Michael G. Hartley
Assistant Examiner — Jagadishwar R Samala
(74) Attorney, Agent, or Firm — Hoffmann & Baron, LLP

(57) ABSTRACT

A process for purifying a compound of formula 1,

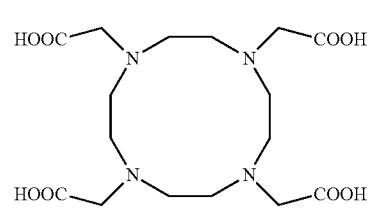

Formula 1 includes the following steps: a) adding an acid to an aqueous solution of the compound of formula 1, including salts and hydrates thereof so as to obtain a slurry having a pH≤3; and b) filtering the slurry and at least one time washing the obtained precipitate with a liquid comprising water; and c) dissolving the precipitate obtained in step b) in water to obtain an aqueous solution; and d) filtering of the solution obtained in step c) over a nanofiltration membrane having a Molecular Weight Cut Off in the range from 150 to 500 and wherein optionally, between step c) and step d) the pH of the aqueous solution is adjusted to a pH value in the pH range as specified by the manufacturer of the nanofiltration membrane. A process for preparing a gadolinium complex of the purified compound of formula 1 is also disclosed. This gadolinium complex can be used for making a pharmaceutical composition as a contrast agent for magnetic resonance imaging.

17 Claims, 1 Drawing Sheet

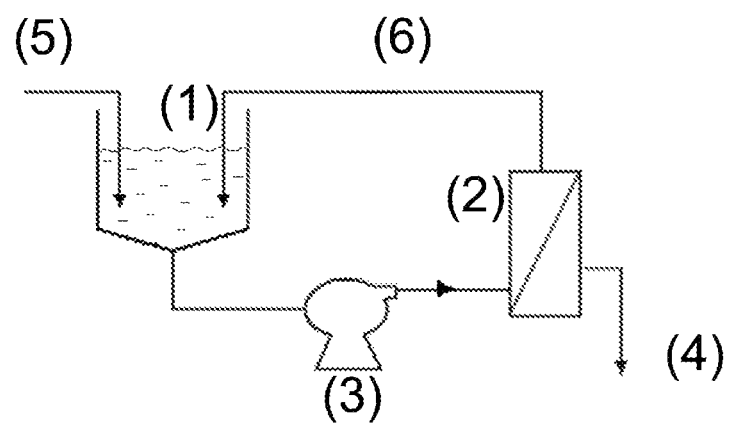

PROCESS FOR PURIFYING 1,4,7,10-TETRA-AZACYCLODODECANE-1,4,7,10-TETRAACETIC ACID

CROSS-REFERENCE TO RELATED APPLICATIONS

This application is a 371 National Stage Application of PCT/EP2015/052033, filed Feb. 2, 2015. This application claims the benefit of European Application No. 14154106.0, filed Feb. 6, 2014, which is incorporated by reference herein in its entirety.

BACKGROUND OF THE INVENTION

1. Field of the Invention

The present invention relates to a process for producing and purifying 1,4,7,10-tetraazacyclododecane-1,4,7,10-tetraacetic acid (DOTA) including salts and hydrates thereof by using nanofiltration techniques. The obtained DOTA is highly purified and thus suitable for being used to produce contrast agents for magnetic resonance imaging. Therefore, the present invention also relates to a process for obtaining metal ion complexes thereof and to a process for obtaining pharmaceutical compositions comprising the metal ion complexes of DOTA.

2. Description of the Related Art

Magnetic resonance imaging (MRI) is a powerful, non-invasive technique used to produce detailed two or three-dimensional anatomical images of tissues in the body. Conventional MRI uses the proton $^1$H as its signal source which is highly abundant in tissues and it has the highest sensitivity of all the biologically relevant nuclei.

Contrast, which makes the differentiation of internal structures possible in the image, arises from how the signal decays and is the difference between the resulting signals from two tissue regions. The route by which the protons release the energy they absorbed from the radio-frequency pulse, thus reducing the transverse magnetisation and causing signal decay, is known as relaxation. In MRI two independent relaxation processes occur simultaneously: spin-lattice or longitudinal relaxation characterised by the time constant $T_1$, and spin-spin or transverse relaxation, characterised by the time constant $T_2$.

Often, when suitable $T_1$- or $T_2$-weighting sequences are used, the natural contrast between two tissues is enough to produce a diagnostically-useful image. However, some conditions do not lead to specific enough changes in the relaxation times of the affected tissue though and then a contrast agent is used to locally change the relaxation times of the diseased tissue, improving the image contrast.

Most contrast agents work by shortening the relaxation times of the water protons in the targeted tissue. $T_1$ contrast agents are based on paramagnetic metal ion chelates which make the tissue appear brighter on the $T_1$-weighted image (positive contrast). $T_2$ contrast agents are usually superparamagnetic iron oxide nanoparticles which create dark spots on the $T_2$-weighted image (negative contrast). $T_1$ agents are the most widely used and the majority of these are based on chelates of the gadolinium ion ($Gd^{3+}$).

To be an effective $T_1$ agent the gadolinium (III) chelate must significantly increase the proton relaxation rates in water. Gadolinium is the seventh element in the lanthanide series and, like the other lanthanide elements, it is most commonly found in the +3 oxidation state, corresponding to the electronic configuration [Xe]4f$^7$. This means that $Gd^{3+}$ has seven unpaired electrons, making it highly paramagnetic i.e. Gd(III) ions have large permanent magnetic moments (due to electron spin angular momentum), but in the absence of an external magnetic field these are randomly oriented. Due to its large size, the Gd(III) ion typically has a coordination number of nine in its complexes. As free ion, gadolinium is very toxic for the tissues but is generally regarded as safe when administrated as a chelated compound.

The level of toxicity depends on the strength of the chelating agent, also known as ligand, chelator or sequestering agent.

Usually these ligands are organic compounds which form two or more separate coordinate bonds with a single central metal ion, in this case, the gadolinium ion, inactivating it and thus reducing or eliminating its toxic effect in the tissues.

Polyaminopolycarboxylic acid compounds are the ligand type of choice because they form exceptionally stable complexes with the Gd(III) ion, which can be explained by a number of reasons. These compounds can be linear (such as pentetic acid or diethylene triamine pentaacetic acid also named as DTPA) or macrocyclic (such as 1,4,7,10-tetraazacyclododecane-1,4,7,10-tetraacetic acid, DOTA). DOTA is used as the ligand in the synthesis of the MRI contrast agent gadoterate meglumine ([Gd(DOTA)(H$_2$O)](meglumine)).

Several synthetic routes for the production of DOTA have been proposed, namely by Stetter, Hermann; Wolfram Frank (1976)—"Complex Formation with Tetraazacycloalkane-N, N',N'',N'''-tetraacetic Acids as a Function of Ring Size". *Angewandte Chemie International Edition in English* 15 (11): 686), by R. Delgado & J. J. Fraústo da Silva—Talanta, Vol. 29, pp. 815-822, Issue 10, 1982, and by J. F. Desreux—Inorg. Chem. 1980, 19, pp. 1319-1324.

The preparation of DOTA was first reported in 1976 by Stetter & Frank (full ref. above) through the reaction of 1,4,7,10-tetraazacyclododecane with chloroacetic acid in aqueous alkali medium to obtain DOTA wherein the resulting inorganic salts were separated and purified by treatment with an ion-exchange column Dowex 2×8.

The method most widely reported in the literature is typified by Delgado et al. (full ref. above), where cyclen is reacted with chloroacetic acid under aqueous basic conditions (pH=~10) to form DOTA, which is crystallised by acidifying the cooled DOTA solution to pH 2 with hydrochloric acid and placing it in the refrigerator overnight.

Desreux (full ref. above) also reported a similar procedure, but specified sodium hydroxide as being the base used, with a reaction temperature of 80° C., and stated that upon acidification DOTA precipitates out of solution at pH 2.5.

E. Clarke & A. Martel (1991)—Inorganica Chimica Acta, 190, pp 27-36), describes the preparation of DOTA by alkylation of cyclic tetraamine ligands with bromoacetic acid at a controlled pH between 11.2 to 11.3 being the resulting product recovered by treatment with a ion-exchange column as ammonium salts followed by treatment with a potassium cation solution at pH of 11.5 and vacuum concentration. The resulting ligands were then reprotonated by addition of HCl and isolated by recrystallization from hot water. Dota is obtained as a mixture of 1/1.1 mole/mole with KCl.

WO9905128 discloses a process for producing DOTA compounds by 2 step-alkylation wherein the alkylation agent is preferably bromoacetic acid but also includes chloroacetic acid, in aqueous solution at a basic pH with an excess of said alkylation agent, followed by hydrolysis and purification with ion exchange resins and with an optional recrystallization step in order to obtain highly purified DOTA compounds. In particular, WO9905128 discloses a multistep process for the preparation of DOTA starting from:

a) an alkylation reaction of a 2a,4a,6a,8a-decahydrotetraazacyclo pentacenaphthylene with an acid in aqueous solution and at a basic pH, followed by
b) a second alkylation reaction with a different alkylating agent, and by
c) the hydrolysis of any ester groups, and wherein the amount of the first alkylating agent used in step a) varies between 2-2.3 mol of reagent per mol of substrate and from 2-3 mol in step b) and the reaction temperature varies from room temperature to 80° C., depending on the reactivity of the alkylating agent.

To be able to be eventually used as a suitable contrast agent comprising gadoterate meglumine, the concentrations of process impurities present in the raw DOTA (both organic and the inorganic) must be removed or significantly reduced. This is so that the purified DOTA meets the strict specifications for use in a contrast agent or else it will not be approved for sale by the relevant medicine regulatory body as it will not be considered safe enough for human use. Therefore a series of purification steps must be employed to remove these impurities without introducing too high a concentration of a new impurity or residual solvent, as these must also meet the specifications.

However, the crude DOTA resulting from the above mentioned processes is still highly contaminated with organic and inorganic impurities, in particular with chloride and sodium ions, and the conventional purification steps using ion-exchange resins, as disclosed above, only solves this problem in some extent.

In fact, G. Hernandez, M. F. Tweedle and R. G. Bryant, Inorg. Chem., 1990, 29, 5109-5113, disclose the synthesis of the sodium salt of $[Gd(DOTA)(H_2O)]^-$ $(Na[Gd(DOTA)(H_2O)] \cdot 4H_2O)$. However, this compound is unsuitable for use as a contrast agent as it contains sodium. Nevertheless, the synthetic procedure herein disclosed highlights that high temperatures (90° C.) and long reaction times (6.5 h) are required to successfully react DOTA and gadolinium oxide ($Gd_2O_3$, an ionic salt which is the source of the gadolinium ion) together to form the thermodynamically stable $[Gd(DOTA)(H_2O)]^-$. This can be accounted for by the very slow kinetics of formation of the complex.

Purification of DOTA by using resins has been described in the patent application EP13152873.9. In this document a process is disclosed that uses resins combined with specific washes allowing obtaining good yields of purified DOTA. However, said process is time consuming and uses chemicals and other consumables, such as resins, ammonia, formic acid and produces a large volume of waste solvents which have to be removed in later stages of the process making this process expensive and difficult to be automated due to the several sequential steps.

WO2013/76743 discloses a process for purifying polyaminocarboxylate compounds without using ion-exchange resins by isolating them under very acidic conditions and purification of the obtained salts by recrystallization with water or water solvent mixtures. However, despite the good quality of the obtained product the yields are rather low.

Nanofiltration is used to remove monovalent ions from higher valent ions and from higher molecular weight organic compounds (see Van der Bruggen, B. and Geens, J. (2008)—Nanofiltration, in Advanced Membrane Technology and Applications (eds N. N. Li, A. G. Fane, W. S. W. Ho and T. Matsuura), John Wiley & Sons, Inc., Hoboken, N.J., USA. doi: 10.1002/9780470276280.ch11).

WO2011054480 shows how Gadobutrol can be prepared by reacting the ligand with Gadolinium salts and removing the counterions by nanofiltration, using a ceramic membrane with a MWCO of 200. This technique is only suitable for purifying the complex and does not provide a solution for DOTA. This method is however not suitable for removing high molecular weight compounds which were formed during the making of the Butrol ligand.

In the Journal of Membrane Science 279 (2006) 446-452, A. Sorin describes how polyaminocarboxylic acids such as DOTA can be rejected by charged nanofiltration membranes. Depending on the pH, the compound is retained, however as a cation or anion. The anionic or cation form of DOTA is not suitable for to be used in contrast agents. In neutral form it is not rejected by the membrane having a MWCO estimated at 2500 and hence this process is not suitable for removing said compounds from ionic contaminants.

It is thus desirable to obtain an optimized and efficient process for the purification of crude DOTA which ensures not only high yields of this compound, preferably at least 50% relative to the amounts of the starting reagents used, but also ensures a DOTA of a suitable purity to be used in the preparation of contrast agents and in a form that was easy to work with.

The present invention discloses a process for purifying DOTA including salts and hydrates thereof by using nanofiltration techniques allowing obtaining purified DOTA with high yields and in highly purified form.

SUMMARY OF THE INVENTION

Preferred embodiments of the present invention provide a method for purifying DOTA, represented by the general formula (I), including salts and hydrates thereof, for obtaining high yields and a high purity in a simple, straightforward and reliable process.

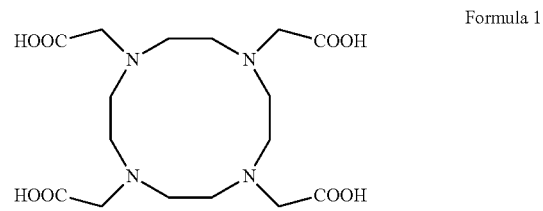

Formula 1

Preferred embodiments are realised by providing a process for purifying DOTA compounds as defined below.

Other preferred embodiments of the invention provide a process for purifying DOTA without the need for a pH adaptation of the solution to be in the pH range as specified by the manufacturer of the nanofiltration membrane as defined below.

Other preferred embodiments of the invention provide a process for producing gadolinium complexes comprising DOTA, as defined below.

Further advantages and preferred embodiments of the present invention will become apparent from the following description and the dependent claims.

BRIEF DESCRIPTION OF THE DRAWINGS

FIG. 1: The set-up of the diafiltration process.
(1) Feed tank
(2) Cross-flow cell with nanofiltration membrane
(3) Feed pump
(4) Permeate stream (5) Diafiltration buffer to keep the volume in the feed tank constant by adding water or a raw DOTA solution at a flow equal to the permeate flow.
(6) The retentate is recycled into the feed tank

DETAILED DESCRIPTION OF THE PREFERRED EMBODIMENTS

The present invention relates to a process for purifying the compound of formula 1, including salts and hydrates thereof, hereafter called DOTA. The steps of this process are described in § B to C. In § A, preparation methods of DOTA are described.

A. Preparing DOTA

There are several ways to prepare DOTA which can be purified according to a process of the present invention. In a preferred embodiment, DOTA can be produced by reaction of cyclen (1,4,7,10-tetra-azacyclododecane) with a haloacetic acid in basic conditions, at a pH≥10, by addition of a base. This base (in solid form or as a concentrated solution of preferably at least 25 (wt.) %) is added slowly to the reaction mass by maintaining preferably the internal temperature at 10° C. An excess of the haloacetic acid can be used in this step, preferably in an amount of at least 4 equivalents and more preferably between 5 to 6 equivalents with regard to the initial amount of the cyclen. In this reaction one equivalent corresponds to one mole per mole ratio. According to the cited prior art, this step is normally performed at a temperature of approximately 80° C. However, it was found that by using an excess of haloacetic acid according to the present invention, lower temperatures may be used. Therefore, in the scope of the present invention, this step can be performed at a temperature ranging from 0 to 100° C., preferably from 0 to 65° C. and more preferably from 0 to 30° C. In a preferred embodiment, the haloacetic acid is chloroacetic acid, bromoacetic acid or iodoacetic acid and more preferably chloroacetic acid.

As in the prior art, the reaction can be performed at pH values of about 10. It was surprisingly found that if the reaction was performed at a pH≥13 no adverse effects were observed and at this pH, the pH has not to be constantly monitored as described in the prior art. Hence the synthesis procedure is easier to operate. Therefore, in a preferred embodiment of the present invention, this step of the DOTA synthesis is performed at a pH≥13 by addition of the base at the start of the reaction. The base can be added in excess, of at least 2 times the amount of the haloacetic acid present in the reaction, namely by using amounts ranging from 8 to 16 equivalents, preferably between 10-12 equivalents with relation to the cyclene. In the scope of the present invention, preferably a strong base is used. With a strong base is meant a basic chemical compound that deprotonates very weak acids in an acid-base reaction and is commonly recognized as a conjugated base of an acid with pKa of at least 13. Suitable examples are alkali metal hydroxides, such as KOH, NaOH, LiOH, RbOH or CsOH and organic non-nucleophilic bases such as 1,1,3,3-tetramethylguanidine. In a most preferred embodiment of the present invention, NaOH or LiOH is used as the base.

The reaction mass is then slowly warmed up to 25° C. and stirred for at least 7 h, most preferably at least 20 h, even more preferably at least 24 h.

Other synthetic routes for preparing DOTA which can be purified by the process of the present invention, are disclosed in "Complex Formation with Tetraazacycloalkane-N,N',N'',N'''-tetraacetic Acids as a Function of Ring Size", by Stetter, Hermann; Wolfram Frank (1976), *Angewandte Chemie International Edition in English* 15 (11): 686), Talanta, Vol. 29, pp. 815-822, Issue 10, 1982, by R. Delgado & J. J. Fraústo da Silva, Inorg. Chem. 1980, 19, pp. 1319-1324 by J. F. Desreux, WO9905128 and in Example 1 of US2014323719.

B. Precipitation and Washing of DOTA

The purification process according to a preferred embodiment of the present invention starts with preparing an aqueous solution of the DOTA which has to be purified. The reaction mixture as obtained in § A is such a suitable aqueous solution of DOTA. The removal of impurities and ions from the aqueous solution of DOTA by means of filtration over a nanofiltration membrane has been found not to be successful. The concentration of the ions in the obtained retentate is much too high in order to be used for the production of contrast agents. Besides this problem, the yield of DOTA is very low due to the insufficient retention of the DOTA. After extensive research, it has been found that prior to the filtration over a nanofiltration membrane, additional steps including precipitation, filtration and washing the precipitate are required.

The precipitation of DOTA is performed by addition of an acid to the reaction mixture until a pH≤3 is achieved. The obtained mixture of solution and precipitate is called hereafter slurry. Preferably an inorganic acid is used to achieve a pH≤3. Suitable inorganic acids are HCl, $H_2SO_4$, $HNO_3$, HBr, HI or $HClO_4$. Besides inorganic acids, organic acids such as p-toluenesulfonic acid and methanesulfonic acid may also be used.

The slurry may be subjected to a heating step and cooling step to obtain a more compact, more crystalline precipitate that is easier to wash. Hence an improved yield and purity of the precipitated DOTA are obtained. This is performed by heating the slurry at a temperature ranging from 50 to 100° C., preferably 50 to 70° C., more preferably 50 to 60° C., for a time period of at least 5 minutes, in order to dissolve the precipitate and obtain a clear solution. Then the solution is cooled at a temperature ranging from 5 to 25° C., preferably 5 to 15° C., more preferably 5 to 10° C., for a time period of at least 5 minutes, to obtain DOTA in the form of a salt depending on the strong inorganic acid selected for lowering the pH of the solution, such as DOTA hydrochloride or other salt.

The final pH of the slurry is ≤3 and can be even less than 0.5. At this low pH values the precipitated DOTA is found in its fully protonated form $(H_2L)^{2+}$ or $(H_3L)^{3+}$ wherein L refers to the ligand DOTA. DOTA in its fully protonated form has counterions, such as chlorides, introduced by the reaction with the acid, and which are electrostatically bound to it, so that its form can be expressed as $H_2L(X)_{2/n}$, wherein X refers to the counterions and n refers to the charge of the counterion. In the case of chloride counterions, the salts of DOTA are denoted hereafter as DOTA bis hydrochloride or DOTA tris hydrochloride. Apart from the negative counterions the precipitated DOTA is also contaminated with cations introduced by the reaction with the base that precipitate out alongside with the DOTA salt.

The slurry is filtered and dry sucked. Any filter can be used to filter the slurry. Suitable examples are filter wool, made of polyethylene terephthalate, polypropylene or nylon, synthetic sponges or foams, various ceramics and sintered glass. The filter material is preferably stable at the pH range of the slurry.

Following the filtration of the precipitate, a washing step is performed. This can be done with a mixture of water and a water miscible low boiling organic solvent in a weight ratio ranging from 1:1.5 to 1:5, preferably in a weight ratio ranging from 1:2 to 1:4. Water miscible low boiling organic solvents are solvents having a boiling temperature preferably lower than 85° C. Suitable examples of water miscible low boiling organic solvents are acetone, ethanol, methanol, iso-propanol, butanone, methyl acetate, ethyl acetate, acetonitrile or THF. The type of water miscible low boiling organic solvent and the ratio in the mixture of water and water miscible low boiling organic solvent used in the washing step can be selected by optimisation wherein the dissolution of the precipitate is minimized and the removal of the contaminating cations and anions is maximised. In a preferred embodiment of the present invention, acetone or ethanol is used as the water miscible low boiling organic solvent.

In this way a DOTA can be obtained that has already a low cation content (<0.5 (wt.) %), but which is still not pure enough to be a suitable reagent for producing contrast agents. This DOTA is hereafter called raw DOTA.

C. pH Adjustment and Nanofiltration

The raw DOTA as obtained in § B is now purified by using nanofiltration membranes. Therefore an aqueous solution of the raw DOTA has to be prepared. A concentration range from 0.1 to 20 (wt.) % is suitable, preferably from 1 to 5%. If the DOTA used is in a protonated form such as DOTA hydrochloride, the obtained aqueous solution of the raw DOTA is acidic. If the pH of the obtained aqueous solution is outside the pH range specified by the manufacturer of the selected nanofiltration membrane, it has to be adjusted to a value within this range. This pH range of a nanofiltration membrane corresponds to the pH range in which the manufacturer of the membrane guarantees substantially no deterioration of the membrane during continuous operation. The values of said pH range of the nanofiltration membrane are specified in the technical sheet provided by the manufacturer.

The adjustment of the pH of the aqueous solution of the raw DOTA can be performed by adding a base, an acid or by diluting the solution with water. Any base is suitable to increase the pH of the aqueous solution of DOTA in its protonated form such as e.g. DOTA bis hydrochloride. Limitation of the concentration of the raw DOTA is also a possibility of achieving a pH of the aqueous solution within the pH range of the nanofiltration membrane as specified by the manufacturer. A limited concentration of DOTA in order to avoid a pH value outside the range specified by the manufacturer of the nanofiltration membrane has the disadvantage that the starting concentration is reduced, which reduces the productivity of the filtration process. To obtain satisfactory results in the nanofiltration process the washing of the precipitate is preferably optimised so that a cation content in the aqueous solution after making the solution of the raw DOTA and after the pH adaptation, is preferably less than 100 ppm, preferably less than 60 ppm, more preferably less than 30 ppm in weight. This optimisation is achieved by the selection of the water miscible low boiling organic solvent, selection of an optimal ratio of water/water miscible low boiling organic solvent and the number of the washing steps performed.

Raw DOTA, salts and hydrates thereof as obtained via the precipitation and washing steps can now be purified in a very efficient way by using nanofiltration membranes with specific molecular weight cut-off (MWCO) thus removing the inorganic ions and other impurities from the larger organic molecule DOTA. Experiments with membranes having a molecular weight cut-off (MWCO) below the molecular weight of the DOTA to be purified, show a retention of the DOTA in the retentate whilst low molecular inorganic ions, such as chloride, sodium, bromide, potassium, etc., are removed via the permeate. Suitable nanofiltration membranes for the purification of the raw DOTA solution are the ones with a MWCO in the range from 150 to 500, preferably from 200 to 300, such as TFC SR100 and SelRO MPS-34 from Koch Membrane Systems, Inc. (USA) or TS40 from TriSep Corporation (USA) or any other membranes with comparable MWCO.

Filtration by nanofiltration membranes can be done according to different techniques. A preferable technique for the purification of raw DOTA according to a preferred embodiment of the invention is the diafiltration technique wherein the solution of the raw DOTA is pumped from the feed tank tangentially along the surface of the membrane (also called tangential flow filtration or cross-flow filtration). The retentate is then fed back to the feed tank. The design of a preferable embodiment of the diafiltration is shown in FIG. 1. The diafiltration process for purifying DOTA can be done in i) the concentration mode (CM), ii) the constant volume mode (CVM) or iii) the variable volume mode (VVM). In the CM, no addition of liquid is done to the feed tank and the concentration of the DOTA in the retentate increases. In the CVM, the volume of the feed tank is kept constant mostly by adding water further washing away the ions from the raw DOTA solution. The third mode combines the 2 other modes to optimise the filtration process.

In a tangential flow filtration process, the filtrate flux (=permeate flow rate normalized for the area of the membrane), is proportional to the pressure difference over the membrane and is called the Trans Membrane Pressure (TMP). The optimal TMP has to be determined for each membrane. The optimum TMP is determined by changing the TMP (bar) at constant feed and measuring the permeate flow (g/min). The optimum TMP is at the "knee" of the curve where the filtrate flow increases with increasing TMP up to a point where it levels off. Working outside the working pressure area can have an irreversible effect, such as mechanical damage, on the membrane behaviour. Suitable pressures in function of the membrane properties used according to known methods, are in the range from 3 to 60 atm. Under these conditions a filtrate flow is created containing inorganic ions and only a very small portion of DOTA is found in the permeate, showing that a good yield is possible.

To monitor online the filtration process, two conductivity meters can be used. A conductivity measuring probe is set in the retentate tank, which will represent a decrease in conductivity and consequently a decrease in concentration of the ions. The second conductivity measuring probe is placed on the permeate flow, where the same decrease is monitored. If the conductivity is decreased to a desired level, the filtration is stopped. Other online or even offline analytical techniques can be used to monitor the level of ions and other impurities in the retentate such as ion-selective electrodes and titration.

When filtering a raw DOTA-solution which is neutralized with a base, for example NaOH or LiOH, in order to obtain a solution with a pH value within the allowable pH range of the selected nanofiltration membrane range as specified by the manufacturer, it is observed that the DOTA is less well retained by the membrane and can be found in the permeate. Although this effect is not completely understood, it is beneficial to keep the concentration of the ions, more specifically the cations in the raw DOTA solution as low as possible by limiting the addition of inorganic bases. Preferably the concentration of the cations in the solution has to be lower than 100 ppm (wt.), preferably lower than 60 ppm (wt.), more preferably lower than 30 ppm (wt.). Achieving a pH value within the pH range specified by the manufacturer of the nanofiltration membrane can therefore be done by further dilution of the solution with water of the raw DOTA or limiting the concentration of the raw DOTA, especially if the raw DOTA is in its fully protonated form such as e.g. DOTA bis hydrochloride and/or DOTA tris hydrochloride. The disadvantage of diluting is a lower efficiency of the purification process because the concentration of the DOTA has to be increased again later on, or by a longer diafiltration time (preferably in the CM) or by the evaporation of water.

Preferably, the nanofiltration is performed by addition of water as diafiltration buffer to the retentate and continuing the diafiltration keeping the volume constant or even concentrating the solution. In a preferred embodiment of the invention, the solution of the raw DOTA is diafiltered, in a first phase with extra feed of a raw DOTA solution as diafiltration buffer and in a second phase with pure water. As the pH of the retentate increases during the diafiltration process of a raw DOTA solution with DOTA in its fully protonated form such as DOTA bis hydrochloride and/or DOTA tris hydrochloride, a more concentrated raw DOTA solution than the raw DOTA solution at the start, can be added as diafiltration buffer, hence increasing the efficiency of the whole filtration process. This increase in efficiency of the filtration process can compensate the loss in efficiency due to the dilution of the raw DOTA solution in order to achieve a pH value compatible with the membrane. Alternatively, a solution of an electrolyte or acid such as formic acid in water can be used prior to the diafiltration with pure water to improve removal of one of the ions.

Although the filtration process over a nanofiltration membrane can be performed at room temperature, a higher temperature is beneficial because it increases the permeate flow, hence increasing the productivity of the process. Preferably the temperature of the nanofiltration is between 10 and 90° C., more preferably between 20 and 70° C.

When the concentration of the ions and impurities has reached a required level in the retentate, the filtration process is ended. In the obtained solution of purified DOTA, the concentration of the DOTA can be increased via diafiltration in CM or via evaporation of the water to a concentration between 5 to 20 (wt.) %, more preferably between 5 to 15 (wt.) %. After increasing the concentration, the DOTA can be precipitated by adding a water miscible low boiling organic solvent to the concentrated solution. Water miscible low boiling organic solvents are solvents having a boiling temperature preferably lower than 85° C. Suitable examples of water miscible low boiling organic solvents are acetone, ethanol, methanol, iso-propanol, butanone, methyl acetate, ethyl acetate, acetonitrile or THF. Preferably acetone, ethanol, methanol or iso-propanol is used as low boiling organic solvent. The addition of the low boiling organic solvent to the DOTA solution can be done while stirring the solution. Speed of the addition and temperature is not critical in obtaining the precipitate. The precipitated DOTA can be filtered and washed with a low boiling organic solvent and dried. The drying can take place in a vacuum dryer or ventilation dryer.

D. Making of a Gadolinium Complex.

The purified compound of formula 1 can be used to make a gadolinium complex by adding a salt or oxide of gadolinium to an aqueous solution of the purified compound of formula 1 so as to obtain complexation of the gadolinium by the purified compound of formula 1.

The DOTA of high purity obtained as described above can be used as the ligand in the formation of the contrast agent gadoterate meglumine, $[Gd(DOTA)(H_2O)]$(meglumine). In a first step, the DOTA-Gd complex has to be made.

For this purpose, a gadolinium compound, preferably $Gd_2O_3$ is added to an aqueous solution of purified DOTA obtained according to a process of the present invention so as to obtain complexation of the gadolinium by the purified DOTA. Preferably an excess of DOTA, most preferably in a molar ratio slightly over 2:1 is used to form an aqueous solution of a complex DOTA-Gd. The temperature of the reaction solution required to form the complex is in the range from 80 to 120° C., preferably from 90 to 100° C., more preferably at a temperature of approximately 95° C. As the kinetics of formation of the complex are very slow, the reaction typically takes 2 to 8 h, preferably from 3 to 6 h, more preferably approximately 4 h.

During this time the pH of the reaction solution typically decreases from ~3 to ~1.5-1.6. In order to complex the Gd(III) ion by the DOTA, the DOTA must become fully deprotonated, which releases hydrogen ions into the solution.

E. Making a Pharmaceutical Composition Based on the Contrast Agent Gadoterate Meglumine ($2^{nd}$ Step).

After allowing the solution obtained in § D. to cool to between 40 and 50° C., N-methyl-D-glucamine (meglumine) is added to balance the negative charge of the complex. Meglumine is added until the pH of the solution is between 6.9-7.8, to meet the pH range required to allow the solution to be safely injected as contrast agent. Meglumine is used as an excipient in many drugs and can even be present in the final solution in excess because it can be well tolerated by the body. After stirring for about half an hour, to ensure the reaction has gone to completion, the reaction solution is allowed to cool to room temperature and is filtered.

The obtained permeate was analysed by combined liquid chromatography with mass spectrometry (HPLC-MS) and was found to contain gadoterate meglumine, showing that the quality of DOTA being synthesised and purified can successfully be used to synthesise a solution of the contrast agent. The DOTA-Gd complex can be easily identified on the electron spray ionisation (ESI) mass spectrum from the collection of peaks 1 m/z (particle mass (amu) per charge) value apart, centred at m/z 560. There are a number of $[M+H]^+$ peaks corresponding to the dehydrated complex because gadolinium has six stable isotopes, five (155Gd, 156Gd, 157Gd, 158Gd and 160Gd) of which all have relative abundances greater than 14%. Meglumine is also evident on the mass spectrum with a $[M+H]^+$ peak at m/z 196.

Specific preferred embodiments will now be described in detail. The examples are intended to be illustrative and the claims are not limited to the materials, conditions or parameters set forth in the examples;

EXAMPLES

The following methods and materials are used in the examples described below.
1. Methods
A. Purity and Assay by HPLC The content of 1, 4, 7, 10-tetraaza-cyclododecane and DOTA was determined by reversed phase HPLC (High Performance Chromatography) with a gradient program and a DAD (Diode Array Detection). The purity of DOTA is expressed as the ratio of the area of the peaks, with regard to total peak area in %. The assay of DOTA is expressed in (wt.) % and is measured by using a standard sample of DOTA (obtained according to the International Conference on Harmonisation (ICH guidelines)).

The chemicals and reagents used are:
Acetonitrile: HPLC grade
Water: HPLC grade or Milli-Q-water
Orthophosphoric acid: HPLC grade
Potassium dihydrogen phosphate: AR grade
The apparatus used is an Agilent 1100/1200 series HPLC system with UV DAD detector, or equivalent.
The chromatographic parameters were:
Column: Prevail Organic Acid, (250×3.0) mm, 5.0 μm
Column Temperature: 30° C.
Detector Wavelength: 195 nm
Pump Configuration: Gradient
Flow rate: 0.44 mL/min
Injection Volume: 5 μL
Run Time: 40 min
Mobile phase A: 20 mM $KH_2PO_4$ in water at pH 2.5 using Diluent (see below)
Mobile phase B: Acetonitrile:Mobile phase A (volume ratio of 60:40)
Mobile phase C: Acetonitrile:Water (volume ratio of 60:40)
Mobile phase D: Acetonitrile:Water (volume ratio of 90:10)
Diluent: 0.1 (wt.) % Orthophosphoric acid in water
The gradient used, is summarised in Table 1:

TABLE 1

| Time (min) | Mobile phase A (%) | Mobile phase B (%) | Mobile phase C (%) | Mobile phase D (%) |
|---|---|---|---|---|
| 0 | 100 | 0 | 0 | 0 |
| 10 | 100 | 0 | 0 | 0 |
| 20 | 50 | 50 | 0 | 0 |
| 21 | 0 | 0 | 100 | 0 |
| 24 | 0 | 0 | 100 | 0 |
| 25 | 0 | 0 | 0 | 100 |
| 32 | 0 | 0 | 0 | 100 |
| 33 | 100 | 0 | 0 | 0 |
| 40 | 100 | 0 | 0 | 0 |

Retention times were for DOTA: 4.6 min, for 1,4,7,10-tetraaza-cyclododecane: 2.7 min. and for chloroacetic acid: 6.9 min.

B. Determination of Chloride Content in DOTA by Potentiometric Titration.

The solution of the sample, obtained by dissolving 50 mg of solid DOTA in a mixture of 20 mL water and 80 mL acetic acid, is titrated with 0.001M $AgNO_3$ using a Mettler DL 25 potentiometric auto titrator. The chloride content is expressed as ppm (wt.) with respect to the weight of DOTA, unless otherwise specified.

C. Determination of Sodium and Lithium Content in DOTA by ICP-OES (Inductively Coupled Plasma—Optical Emission Spectrophotometry).

The sodium and lithium content is expressed as ppm (wt.) or as (wt.) % with respect to the weight of DOTA. The lithium content in the aqueous solution of the raw DOTA is also determined by means of ICP-OES.

D. Determination of Sodium Content by Measurement with an Ion Selective Electrode.

The sodium content in the aqueous solution of the raw DOTA is measured with a Metrohm 781 pH/ion meter connected to a sodium glass electrode and an Ag/AgCl reference-electrode. The sample preparation is performed as prescribed in the Manual Ion-selective electrodes (ISE), Metrohm A G, Herisau, Switzerland, 2010. The results are given in ppm (wt.) or as (wt.) %.

E. Determination of the Moisture Content of DOTA.

Water content of DOTA is determined with a modified Karl-Fischer titration by heating a sample at 200° C. in a drying oven, absorbing the removed water in dry methanol. The water absorbed in the methanol is titrated with Hydranal Composite 5 KF reagent, using a Metrohm Titrando 835 with a 774 Oven Sample Processor.

F. Determination of 1,1,3,3-Tetramethyl Guanidin (TMG) in DOTA

The 1,1,3,3-tetramethyl guanidin (TMG) content in DOTA is determined via H-NMR.

G. Determination of the Optimal TMP for Each Membrane.

The optimum TMP was practically determined by changing the TMP (bar) at a constant feed (=35 g/min) and measuring the permeate flow (g/min). The optimum TMP is at the "knee" of the curve where the filtrate flow increases with increasing TMP up to a point where it levels off. The optimum TMP was determined with deionised water.

2. Materials

All reagents used to prepare DOTA were obtained commercially and used as received:
1,4,7,10-tetraaza-cyclododecane (cyclen) from IS Chemical technology.
Chloroacetic acid from S.r. Drugs & Intermediates Pvt. Ltd
$Gd_2O_3$ from Rhodia.
N-methyl-D-glucamine (meglumine) from Merck.
Acetone from Rekha Chemical Corporation.
Lithiumhydroxide monohydrate from Merck
1,1,3,3-tetramethyl guanidin (TMG) from Acros Chemicals For the nanofiltration experiments, deionised water was used with a conductivity of less then 5 μS/cm. All nanofiltration membranes used were obtained commercially and used as received. The pH range disclosed hereafter is specified by the manufacturer of the membranes.

SelRO MPS-34, from Koch Membrane Systems, Inc., pH range: 0-14;
TS 40, from TriSep Corporation, pH range: 2-11.
Koch TFC-SR100, pH range: 4-10
The pressure ranges of the membranes as specified by the manufacturer are:
Trisep TS40: 3-14 atm.;
Koch TFC-SR100: 14-41 atm.;
Koch SelRO MPS-34: 15-35 atm.;
The nanofiltration cell used, is a teflon CF042 cell obtained from Sterlitech. The filtration area is 42 $cm^2$ and the maximum pressure for this cell is 29 atm.

An aqueous solution of NaOH (29 (wt.) %) was obtained from M. R. Fine Chem., an aqueous solution of HCl (36 (wt.) %), was obtained from RFCL Limited and diluted using deionised water as required.

In Process Control (IPC) is using HPLC according to the method of § 1. The values are expressed as the ratio (in %) of the area of the peaks, with regard to the total peak area, to report values for cyclen as starting material and DOTA as product.

Conductivity is measured using a conductometer from Metrohm using a standard conductivity cell; the result is expressed in μS/cm.

The yield of the raw DOTA is reported as the number of moles of isolated product (DOTA bis hydrochloride, without correcting for assay) per number of moles of cyclene starting material. The yield of DOTA in the purification step is reported as the weight of isolated pure DOTA per weight of raw DOTA input corrected for the assay.

3. Preparation of DOTA to be Purified

Seven batches of DOTA were prepared. Batch B-01 was prepared by adding chloroacetic acid (54.86 Kg, 580.48 mol) to a solution of 1,4,7,10-tetraaza cyclododecane (20 Kg, 116.1 mol) in water (120 L) and the reaction mixture was cooled to 5±5° C. A solution of sodium hydroxide (48.77 Kg in 120 L water, 1219 mol) was added slowly to the reaction mass by maintaining the internal temperature at 10±5° C. The reaction mass was slowly warmed to 25±5° C. and stirred for 20 h. The obtained DOTA batch B-01, according to IPC has a DOTA content of 75.53 (area) %, contains also an intermediate compound (at retention time of 0.84 from the retention time of DOTA) of 1.2 (area) % and a cyclene content of 0.0%.

Batch B-02 was prepared by adding chloroacetic acid (197.48 g, 2090 mmol) to a solution of 1,4,7,10-tetraaza cyclododecane (72.0 g, 418 mmol mol) in water (438 g) and to cool the reaction mixture to 10° C. A solution of NaOH (29 (wt.) % in water, 599.5 g) was added while keeping the temperature between 8 and 13° C. The reaction mass was stirred, heated to 30° C. and kept at this temperature during 22 h.

Batch B-03 was prepared by adding chloroacetic acid (23.16 g, 0.245 moles) to a solution of cyclen (8.44 g, 49 mmole) in 51 mL water. The reaction mixture was cooled at 10° C. and 12.2 g of LiOH powder (0.51 mole) was added at once via a funnel that was rinsed afterwards with 5 g water. A slightly turbid solution was obtained with a pH=9. Then the reaction mixture was heated to 30° C. and stirred for 24 h, during which time the pH did not change.

Batch B-04 was prepared by adding chloroacetic acid (23.16 g, 0.245 moles) to a solution of cyclen (8.44 g, 49 mmole) in 51 mL water. The reaction mixture was cooled at 10° C. and 58.7 g of TMG (1,1,3,3-tetramethyl guanidine, 0.51 mole) was added at once via a funnel that was rinsed afterwards with 5 g water. A slightly turbid solution was obtained (pH=9). Then the reaction mixture was heated to 30° C. and stirred for 24 h, during which time the pH did not change.

Batch B-05 was prepared by dissolving 49 mmoles of the cyclen hydrochloride (15.6 g) into 51.4 mL of water and by adding 23.1 g of chloroacetic acid (245 mol) at a temperature of 10° C. Then 94.6 g of a NaOH solution (29%, 0.686 mol) where added to the reaction mixture and the temperature was raised to 30° C. so as to obtain a clear solution. The reaction mixture was kept at 30° C. during 24 h.

Batch B-06 was prepared by dissolving 49 mmoles of the cyclen hydrochloride (15.6 g) into 51.4 mL of water and by adding 23.1 g of chloroacetic acid (245 mole) at a temperature of 10° C. Then 12.2 g of LiOH powder (0.51 mole) was added at once via a funnel that was rinsed afterwards with 5 g water. A slightly turbid solution was obtained with a pH=9. Then the reaction mixture was heated to 30° C. and stirred for 24 h, during which time the pH did not change.

Batch B-07 was prepared by dissolving 40 mmoles of the cyclen hydrochloride (15.6 g) into 51.4 mL of water and by adding 23.1 g of chloroacetic acid (245 mole) at a temperature of 10° C. Then, 58.7 g of TMG (1,1,3,3-tetramethyl guanidine, 0.51 mole) was added at once via a funnel that was rinsed afterwards with 5 g water. A slightly turbid solution was obtained (pH=9). Then the reaction mixture was heated to 30° C. and stirred for 24 h, during which time the pH did not change.

4. Addition of an Acid to an Aqueous Solution of DOTA (Step a)) and Filtration (Step b)).

From the batch B-01 of the reaction mixture obtained in § 3. a portion of 50 g. was taken. This part is denoted as batch B-01A. 24.6 g of an HCl solution (36 (wt.) %) is added to batch B-01A having a temperature of 5° C. The obtained slurry was filtered on a sintered glass filter. The precipitate on the filter had a high volume and was difficult to wash with water/acetone mixtures due to the slow passage of the liquids.

The remaining part of batch B-01 was cooled to 5±5° C., acidified with 150 L of an HCl solution of 36 (wt.) % and stirred at 5±5° C. for 10-15 min. A slurry comprising a white solid was obtained. Batch B-01 was further slowly warmed to 25±5° C. and heated to 65±5° C. A clear solution was obtained and the solution was stirred for 10 min at the same temperature. The solution was then cooled to 5±5° C. over a period of 4-5 h. and stirred for 10 min. Again, a slurry was obtained. The slurry was filtered using a polypropylene filter cloth with a mesh size of 40 μm and suck dried for 10 min. The reactor was rinsed with a mixture of water (62.2 L) and acetone (157.2 L). The wet precipitate was mixed with the mixture of water and acetone used for rinsing the reactor while stirring. The solid was suck dried for 30 min and dried in a ventilated tray dryer at 67±3° C. for 6 h. The obtained raw DOTA batch, RB-01 had a moisture content of 4.8 (wt.) % (after 6 h.) according to IPC. The amount of obtained raw DOTA is 41.6 Kg. The purity by HPLC is 89.74%; the Na-content is 188 ppm; the Cl-content is 19.0 (wt.) %. The assay by HPLC of DOTA is 78.9 (wt.) %.

Batch B-02 was cooled to 5° C., a portion of 200 mL was taken and the pH of this portion was adjusted to 8.1 with an HCl solution (36 (wt.) % in water). This portion is denoted as batch B-02A. The remainder batch B-02 was acidified with 531.1 g of HCl (36 (wt.) % solution in water) while stirring and keeping the temperature at 5° C. At pH=3 precipitation occurred. After completion of the addition, the obtained slurry was stirred for 30 more minutes at 5° C. Then the mixture was heated to 68° C. for 30 minutes to obtain a clear solution. This solution was cooled to 10° C. and stirred at that temperature during 3 h. The obtained slurry was then filtered using a sintered glass filter with a mesh size of 40 μm and the precipitate was mixed and washed 3 times on the filter with in total 675 g of a 2:1 mixture of acetone:deionised water (w/w) while stirring. The moist crystals (134 g) were dried in a ventilated oven at 40° C. until a constant weight is achieved; 117 g of raw DOTA as dry crystals were obtained. The obtained raw DOTA batch, RB-02 had a Na-content of 809 ppm, a Cl-content of 12.7 (wt.) %, a moisture content of 13.4 (wt.) %, and an assay by HPLC of 76.8 (wt.) %.

Batches B-03 and B-04 were cooled to 5° C. and then acidified with 75 g of 36% (w/w) HCl solution while keeping the temperature at 5° C. A slurry with a pH=3 was obtained. This slurry was heated to 70° C. and a clear solution was obtained and after 30 minutes cooled to 10° C. with a cooling gradient of 1° C./min. The white crystals were filtered on a P3 glass filter and suspended during 1 h in a mixture of water (26 g) and acetone (53 g). The crystals where filtered on a P3 glass filter and washed on the filter with a water/acetone mixture containing 26 g of water and 52 g of acetone. From batch B-03 17.3 g of a raw DOTA as a white powder was obtained (HPLC content of 90.5 (wt.) %, Cl-content of 3 (wt.) %, a Li-content lower than 50 ppm measured by ICP-OES, the yield of DOTA is 79 (wt.) %) after drying in a ventilated tray dryer. From batch B-04, 19.05 g of Raw DOTA was isolated (HPLC content 88.4%, Cl-content measured by titration is 15%, the TMG content measured by NMR is lower than 0.4 (wt.) %, the yield of DOTA is 85 (wt.) %).

Batches B-05, B-06 and B-07 were cooled to 5° C. and acidified with 94.3 g of a 36% HCl solution (0.931 moles), yielding a slurry. This slurry was redissolved by heating to 70° C. and kept at that temperature for 30 min. The solution was cooled again to 10° C. with a gradient of 1° C./min and stirred during 1 h. The precipitate was filtered on a P3 glass filter and stirred during 1 h in a mixture of 26 g water and 53 g of acetone. From batch B-05, 17.506 g of DOTA as white crystals where obtained (HPLC content 88.6%, Cl-content is 16%, Na-content is 3887 ppm, the yield=78 (wt.) %) after drying in a ventilated dryer. From batch B-06, 13.74 g of raw DOTA where obtained (HPLC content 86.5%, Cl-content is 19%, Li-content is lower than 50 ppm, the yield is 60 (wt.) %) after drying in a ventilated dryer. From batch B-07, 16.24 g of raw DOTA is obtained (HPLC content 87.5%, Cl-content of 16.3 (wt.) %, TMG-content is lower than 0.1 (wt.) %, and a yield of 88 (wt.) %) after drying in a ventilated dryer.

5. Dissolving the Precipitate (Step c)) and pH Adjustment of the Aqueous Solution if Required.

Aqueous solutions of raw DOTA (S-02 to S-06, see Table 2) were prepared by dissolving parts of the raw DOTA batches RB-01 and RB-02, to obtain concentrations of DOTA and amounts as mentioned in Table 2. Depending on the type of the nanofiltration membrane and the concentration of the raw DOTA, the pH of the solutions had to be adjusted towards a value within the pH range as specified by the manufacturer of the membrane. This pH value was obtained by adding a NaOH solution (29 (wt.) %) to the solution S-02 or by limiting the concentration of the raw DOTA, which behaves acidic because the raw DOTA was present as DOTA bis hydrochloride. Besides the solutions S-02 to S-06, an aqueous solution S-07, in an amount of 1134 g of 2.3 (wt.) % of DOTA was prepared which was to be used as diafiltration buffer. The pH of this solution was 1.6 and was not adjusted.

As a comparative, solution S-01 was prepared by adjusting the pH of the reaction mixture B-02A to 8.1 with 20 g of the HCl solution (36 (wt.) %), and by diluting 97.5 g of this solution with 236.8 g of deionised water to obtain 334 g of an aqueous solution having a concentration of DOTA of 3 (wt.) %. The measured pH of this solution was 8.2, and is within the pH range as specified by the manufacturer of the nanofiltration membrane. The prepared solutions are summarised in Table 2.

6. Filtration of Aqueous Solutions of Raw DOTA Over a Nanofiltration Membrane (Step d)).

The solutions S-01 to S-06 were put in the feed tank before the start of each of the filtration processes. From solution S-03, 375 g solution was put in the feed tank. The diafiltration processes were performed as set-up in FIG. 1, with a feed rate of 35 g/min. and a pressure of 12.5 atm. for the TS40 membrane (using the Prominent Gamma L 1602 pump) or 20 atm. for the SelRO membrane (using the Waters Delta 600 pump). The solutions and installation were kept at room temperature during the filtration process. The volume in the feed tank of the solutions S-01, S-02 and S-06 was kept constant by adding water as diafiltration buffer. In case of the solutions S-04 to S-05, in a first phase, the volume in the feed tank is kept constant by adding the raw DOTA solution of 2.3 (wt.) % DOTA from § 5. as the diafiltration buffer (=CVM) to the feed tank. The total weight of this solution added as diafiltration buffer is displayed in Table 3. In case of the solution S-03, in a first phase, the volume of the feed tank is kept constant by adding the remaining part of the solution S-03 as a diafiltration buffer to the feed tank. After complete addition of the raw DOTA solutions during the diafiltration of S-03 to 5-05, deionised water was added as diafiltration buffer so as to keep further the volume in the feed tank constant. The filtration experiment was continued until the permeate conductivity was less then 250 μS/cm, except for S-01 and S-05. The filtration with S-05 was stopped after 55.5 h. The total permeate of S-02 to S-06 was collected and weighed. The weights are mentioned in Table 3. The filtration loop was rinsed with 200 g of deionised water. 500 g of the obtained retentate from P-02 to P-06, including the rinsing liquid of the reactor was concentrated with a rotary evaporator to yield a moist residue of 8.64 g. This residue was redissolved in water to obtain a solution of 90 g. and precipitated with 180 g of acetone. The precipitate was filtered, first washed with 75 g of acetone:water (2:1 w/w) and then washed with 45 g of acetone and dried in a ventilation drier at 60° C. until a constant weight is achieved. The content of Na, Cl in the solid purified DOTA (P-02 to P-06) and the yields are included in Table 3.

TABLE 2

|  | S-01 (COMP) | S-02 (INV) | S-03 (INV) | S-04 (INV) | S-05 (INV) | S-06 (INV) |
| --- | --- | --- | --- | --- | --- | --- |
| Raw DOTA batch | B-02A | RB-01 | RB-01 | RB-02 | RB-02 | RB-02 |
| Nanofiltration membrane | SelRO MPS-34 | TS40 | TS40 | TS40 | TS40 | SelRO MPS-34 |
| pH | 8.2 | 3.7 | 1.9 | 2.3 | 2.3 | 1.6 |
| pH adjustment by | HCl | NaOH | — | — | — | — |
| Na content in raw DOTA (ppm) | 7 (wt.) %* | 102000 | 185 | 809 | 809 | 809 |
| Cl content in raw DOTA (ppm) | 2 (wt.) %* | 142000 | 142000 | 127000 | 127000 | 127000 |
| DOTA conc. in solution (wt. %) | 3.0 | 2.8 | 1.15 | 0.77 | 0.77 | 2.0 |
| Amount of solution (g) | 334 | 306 | 750 | 300 | 300 | 500 |

*calculated ion concentration in S-01 at the start of the diafiltration process.

TABLE 3

|  | P-01 (COMP) | P-02 (INV) | P-03 (INV) | P-04 (INV) | P-05 (INV) | P-06 (INV) |
|---|---|---|---|---|---|---|
| Weight of raw DOTA solution as diafiltration buffer (g) | — | — | 375 S-03 | 567 S-07 | 567 S-07 | — |
| Concentration of Na-ions in the feed tank at the start of filtration process | 7 (wt.) % | 0.28 (wt) % | 2.4 ppm | 8.1 ppm | 8.1 ppm | 21 ppm |
| Weight of permeate (kg.) | 2.71 | 5.46 | 4.18 | 6.73 | 4.44 | 5.87 |
| End value of the conductivity (μS/cm) | 2800 | 38 | 195 | 110 | 500 | 250 |
| Na content (ppm) | 1700 | 8234 | 37 | 109 | <50 | 629 |
| Cl content (ppm) | 148000 | 31 | 226 | <30 | 490 | 1870 |
| Yield of DOTA (%) | 63 | 35 | 59 | 66 | 85 | 92 |

Purified DOTA from solution S-01 was obtained differently than from solutions S-02 to S-06. The solution S-01 did not show a significant decrease in conductivity during the diafiltration. After 72 h., the diafiltration was stopped. The DOTA could not be isolated from the aqueous solution by the process of concentrating, redissolving and precipitation as it could with the retentate of S-02 to S-06. To determine the yield of the purified DOTA and the content of Na and Cl ions in the DOTA of the comparative example, the retentate of S-01 after attempting isolation as described above, was concentrated and redissolved in 47 g of water, acidified with 29 g of HCl solution (36 (wt.) %), and the obtained slurry was filtered. The precipitate was suck dried and dried in a ventilation oven to obtain 7.1 g of DOTA (P-01).

It can be concluded from the above results that the purification of DOTA based on filtration over a nanofiltration membrane can only significantly reduce the concentration of Na and Cl ions if the DOTA, as obtained by the reaction of 1,4,7,10-tetra-azacyclododecane with a haloacetic acid with a base at a pH≥10, is subjected to preceding purification steps. These purification steps comprise a precipitation by adding an acid to the reaction mixture (step a)), filtrating and washing of the precipitate (step b)) and redissolving the obtained raw DOTA to make an aqueous solution of this raw DOTA (step c)). Indeed, Cl-ion and Na-ion concentrations in purified DOTA, P-01 without these purification steps, are both very high with respect to the other batches.

It is also clear from the results that, if an adjustment of the pH of the aqueous solution of the raw DOTA is required, this adjustment is preferably done by limiting the DOTA bis hydrochlorate concentration prior to the filtration process over a nanofiltration membrane so as to avoid extra cations into the solution introduced by the use of NaOH as the base to adjust the pH. The Na-ion concentration in the purified DOTA batches, P-03 to P-06 where the aqueous solutions of raw DOTA were not subjected to a pH adjustment with a base, is lower than the Na-ion concentration in the DOTA batch P-02.

7. Determination of the Retention Factors for DOTA and for the Ionic Contaminants.

In order to determine retention factions, solutions of DOTA were prepared based on purified DOTA. The purified DOTA was obtained from raw DOTA and purified with ion exchange resins as described in WO2014/114664. From the raw DOTA batch RB-01, 36 kg was dissolved in 540 L of demineralised water, 216 kg of Amberlite IR120(H+) resin (freshly washed with water until the pH of the decantate is higher than 4) were added; the suspension was stirred for 16 h at room temperature; the supernatant was removed and the resin was rinsed with water until the pH of the washing solution is higher than 4 (in portions of 540 L). The resin was stirred with 720 L portions of ammonia solution (3 (wt.) % in water) at room temperature until no more DOTA (less then 2 (wt.) % of the input quantity) showed in the supernatant (Thin Layer Chromatography: water/methanol 8/2, staining with $KMnO_4$). The combined ammonia wash solutions were concentrated by evaporation under vacuum to a 10 (wt.) % solution of DOTA in water. Water (540 L) was added and the solution was concentrated by evaporation in vacuum. This was repeated 3 times.

Subsequently, the DOTA solution (10 (wt.) %) was stirred with Amberlyst A26(OH—) resin (183 kg, freshly washed with 460 L portions of water until the pH was <10) during 6 h at room temperature. The supernatant was removed by decanting and the resin was washed with 460 L portions of demineralised water until the pH of the washing solution was lower than 10. Then, the resin was washed twice with 610 L of 0.02 (wt.) % formic acid in water, the washing solutions were discarded. Next, the resin was washed with 615 L portions of a 1 (wt.) % formic acid solution in water until the DOTA concentration in the washing solution was lower than 0.05 (wt.) %, determined as above. The combined 1 (wt.) % formic acid washes were concentrated in vacuum until a 10 (wt.) % solution of DOTA in water was obtained, 460 L water was added and the solution was concentrated to 10 (wt.) %. This last action was repeated 5 times.

Then 185 L of ethyl alcohol was added. The mixture was concentrated by evaporation under vacuum to a 10 (wt.) % solution Acetone (245 L) was added and the suspension was cooled to 15° C. The precipitate was centrifuged, the cake in the centrifuge was washed with 61 L of acetone and then dried in a vacuum tray dryer at 67° C. and 550 mm Hg till the water content was lower than 10 (wt.) %. The dried DOTA was dissolved in 110 L of water at 45° C., 330 L ethylalcohol were added slowly at 45° C., the mixture was cooled to room temperature and centrifuged; the cake was rinsed with 220 L of ethylalcohol and dried in a vacuum tray drier at 550 mm Hg, first at 25° C. and then at 67° C. until the water content was lower than 10 (wt.) %. After homogenising, 27 kg of purified DOTA were obtained, the Na-content is 5 ppm, the Cl-content is 76 ppm, the formiate-content is 495 ppm, the ammonia-content is 46 ppm. The HPLC purity is 99.97%, the assay is 91.5 (wt.) %.

Solution S-07 was prepared by dissolving 15 g (37.1 mmole) of purified DOTA in 480 g of water and 20 g of a 30 (wt.) % NaOH solution in water was added. Solution S-08 was prepared according to the same way as S-07. Solution S-09 was prepared by dissolving 15 g (37.1 mmole) of purified DOTA in 480 g of water and 3.63 g of LiOH (148.4 mmole) was added. Solution S-10 was prepared according to the same way as S-09.

To determine the retention factors for DOTA and for the ionic contaminants (Na+ or Li+ and Cl−) a different set-up was used: a solution of DOTA and ions was circulated over the membrane and both retentate and permeate were recycled to the feed tank. After 1 h, samples were taken from the feed tank, the retentate and the permeate stream and analysed for DOTA, cationic and chloride content.

The retention factor (in %) for species I is calculated according to formula 2:

$$R_f = 100 \times (1 - [I]_{permeate}/[I]_{retentate}) \quad \text{(formula 2)}$$

wherein:

$[I]_{permeate}$: concentration of the species I in the permeate $[I]_{retentate}$: concentration of the species I in the retentate Solutions S-07 and S-09 were circulated over a SelRO MP34 membrane using a Prominent Hydro type 2 2506 pump at 20 atm and a feed flow of 35 g/min. After 1 h samples were taken from feed, permeate and retentate streams and analysed for DOTA, Na and Cl content. In the feed tank, also pH and conductivity were measured. The results of the measurements are listed in Table 4. Then 3.65 g of a 37% HCl in water was added (37.1 mmol, 1 equivalent with regard to DOTA) and the obtained solution was again re-circulated over the membrane as above. After 1 hour, samples were taken as described before and analysed. This procedure (adding an equivalent aliquot of HCl) was repeated 4 times (in total 5 equivalents of HCl are added). The results are presented in Table 4.

TABLE 4

| Solution | HCl equival. | pH | Conductivity | Permeate flow (g/min) | $R_f$ DOTA | $R_f$ Na/Li | $R_f$ Cl |
|---|---|---|---|---|---|---|---|
| S-07 | 0 | 12 | 13270 | 0.9 | 99.8% | 92.8% | — |
| S-07 | 1 | 9.3 | 14270 | 0.9 | 99.6% | 88.3% | 43.8% |
| S-07 | 2 | 8.7 | 17350 | 0.9 | 99.6% | 70.1% | 49.1% |
| S-07 | 3 | 4.6 | 20200 | 0.9 | 98.0% | 69.8% | 55.9% |
| S-07 | 4 | 3.9 | 22900 | 0.7 | 97.3% | 70.8% | 69.3% |
| S-07 | 5 | 2.1 | 30700 | 0.6 | 98.8% | 72.5% | 75.6% |
| S-09 | 0 | 11.3 | 8690 | 0.8 | 99.8% | 98.2% | — |
| S-09 | 1 | 9.1 | 10800 | 1 | 99.6% | 91.8% | 62.7% |
| S-09 | 2 | 7.2 | 15600 | 1.1 | 99.7% | 66.8% | 28.8% |
| S-09 | 3 | 4.1 | 18000 | 1 | 99.6% | 76.6% | 66.0% |
| S-09 | 4 | 3.2 | 21500 | 0.6 | 99.8% | 78.0% | 69.7% |
| S-09 | 5 | 2.7 | 26100 | 0.5 | 99.6% | 81.3% | 77.9% |

The solutions S-08 and S-10 were circulated over a Trisep TS40 membrane using a Prominent gamma L 1602 pump at 12.5 atm and a feed flow of 35 g/min. After 1 h samples were taken from feed, permeate and retentate streams and analysed for DOTA, Na-, Li- and Cl-content. In the feed tank, also pH and conductivity were measured. The results of the measurements are listed in Table 5. Then 3.65 g of a 37% HCl in water was added (37.1 mmol, 1 equivalent with regard to DOTA) and the obtained solution was again re-circulated over the membrane as above. After 1 hour, samples were taken as described before and analysed. This procedure (adding an equivalent aliquot of HCl) was repeated 3 and 2 times (in total 4 and 3 equivalents of HCl were added). The results are presented in Table 5.

TABLE 5

| Solution | HCl equival. | pH | Conductivity | Permeate flow (g/min) | $R_f$ DOTA | $R_f$ Na/Li | $R_f$ Cl |
|---|---|---|---|---|---|---|---|
| S-08 | 0 | 9.54 | 9491 | 0.92 | 98.4% | 98.0% | — |
| S-08 | 1 | 8.69 | 9390 | 0.96 | 98.7% | 68.1% | −9.8% |
| S-08 | 2 | 4.81 | 9289 | 1.46 | 99.1% | 36.6% | −1.4% |
| S-08 | 3 | 3.56 | 9193 | 1.18 | 99.7% | 38.5% | 31.5% |
| S-08 | 4 | 2.35 | 9102 | 1.07 | 98.8% | 29.6% | 36.4% |
| S-10 | 0 | 9.5 | 9781 | 0.9 | 97.7% | — | — |
| S-10 | 1 | 8 | 9706 | 1.2 | 98.3% | — | −19.7% |
| S-10 | 2 | 4.7 | 9653 | 1.3 | 98.8% | — | −5.6% |
| S-10 | 3 | 4.1 | 9625 | 1.1 | 98.8% | — | 11.4% |

From these results it is clear that the retention for DOTA is better with the SelRO membrane and that in the presence of Li ions the DOTA retention is even higher. The experiments at lower pH show a higher concentration of chloride ions then metal ions in the permeate.

The invention claimed is:

1. A process for purifying a compound of formula 1, the process comprising the steps of:

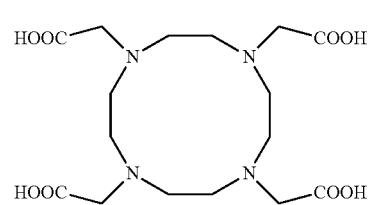

Formula 1 a) adding an acid to an aqueous solution of the compound of formula 1, or a salt thereof, to obtain a slurry with a pH≤3;
b) filtering the slurry to obtain a precipitate, and washing, at least once, the precipitate with a liquid, wherein the liquid is a mixture of water and a water miscible low boiling organic solvent; and wherein the mixture has a water to water miscible low boiling organic solvent weight ratio from 1:1.5 to 1:5;
c) dissolving the precipitate obtained in step b) in water to obtain an aqueous solution; and
d) filtering the aqueous solution obtained in step c) over a nanofiltration membrane having a Molecular Weight Cut Off in a range from 150 to 500 daltons (Da); and
optionally, between step c) and step d), adjusting the pH of the aqueous solution to a pH value in a pH range specified by a manufacturer of the nanofiltration wherein a heating step and cooling step is performed to obtain the slurry.

2. The process according to claim 1, wherein the water miscible low boiling organic solvent is selected from the group of acetone, ethanol, methanol, isopropanol, butanone, methyl acetate, ethyl acetate, acetonitrile, and tetrahydrofuran (THF).

3. The process according to claim 1, wherein the heating step is performed at a temperature in a range from 50° C. to 100° C., for at least 5 minutes, and the cooling step is performed at a temperature in a range from 5° C. to 25° C., for at least 5 minutes.

4. The process according to claim 1, wherein the aqueous solution of the compound of formula 1 in step a) is obtained by reacting 1,4,7,10-tetra-azacyclododecane and a haloacetic acid with a base at a pH≥10.

5. The process according to claim 1, wherein the aqueous solution of the compound of formula 1 in step a) is obtained by reacting 1,4,7,10-tetra-azacyclododecane and a haloacetic acid with a base at a pH≥10.

6. The process according to claim 4, wherein an initial amount of the haloacetic acid is at least 4 equivalents, with respect to an amount of the 1,4,7,10-tetra-azacyclododecane and an amount of the base is at least two times a number of the equivalents of the haloacetic acid.

7. The process according to the claim 4, wherein the haloacetic acid is selected from the group of iodoacetic acid, bromoacetic acid, and chloroacetic acid.

8. The process according to the claim 5, wherein the haloacetic acid is selected from the group of iodoacetic acid, bromoacetic acid, and chloroacetic acid.

9. The process according to the claim 6, wherein the haloacetic acid is selected from the group of iodoacetic acid, bromoacetic acid, and chloroacetic acid.

10. The process according to claim 1, wherein the acid in step a) is selected from the group of hydrochloric acid, hydrobromic acid, hydroiodic acid, sulphuric acid, nitric acid, and perchloric acid.

11. The process according to claim 1, wherein step d) includes a diafiltration process.

12. The process according to claim 11, wherein a portion of the solution obtained in step c) is added as a diafiltration buffer to a feed tank.

13. The process according to claim 1, further comprising the following steps: e) increasing a concentration of the compound of formula 1 in the solution obtained in step d) via diafiltration or evaporation of water so as to obtain a concentration from 5% to 20% by weight; f) precipitating the compound of formula 1 by adding a water miscible low boiling organic solvent to the solution obtained in step e); and g) filtering and drying the precipitate.

14. A process for preparing a gadolinium complex of a compound of formula 1 comprising the steps of: purifying the compound of formula 1 as defined in claim 1; and adding a salt or oxide of gadolinium to an aqueous solution of the purified compound of formula 1 so as to obtain complexation of the gadolinium by the purified compound of formula 1.

15. A process for preparing a gadolinium complex of a compound of formula 1 comprising the steps of: purifying the compound of formula 1 as defined in claim 11; and adding a salt or oxide of gadolinium to an aqueous solution of the purified compound of formula 1 so as to obtain complexation of the gadolinium by the purified compound of formula 1.

16. A process for making a pharmaceutical composition comprising the steps of: purifying the compound of formula 1 as defined in claim 1; adding a salt or oxide of gadolinium to an aqueous solution of the purified compound of formula 1; and adding meglumine to the aqueous solution before or after the addition of the salt or oxide of gadolinium.

17. A process for making a pharmaceutical composition comprising the steps of: purifying the compound of formula 1 as defined in claim 11; and adding a salt or oxide of Gadolinium to an aqueous solution of the purified compound of formula 1; and adding meglumine to the aqueous solution before or after the addition of the salt or oxide of Gadolinium.

* * * * *